United States Patent
Neuman et al.

(10) Patent No.: US 11,389,114 B2
(45) Date of Patent: Jul. 19, 2022

(54) DEVICE TO MEASURE ANALYTES IN THE SKIN

(71) Applicant: FibroTx OÜ, Tallinn (EE)

(72) Inventors: Toomas Neuman, Tallinn (EE); Aram Kazarjan, Tallinn (EE)

(73) Assignee: FIBROTX OÜ, Tallinn (EE)

( * ) Notice: Subject to any disclaimer, the term of this patent is extended or adjusted under 35 U.S.C. 154(b) by 467 days.

(21) Appl. No.: 14/655,850

(22) PCT Filed: Dec. 20, 2013

(86) PCT No.: PCT/EP2013/077734
§ 371 (c)(1),
(2) Date: Jun. 26, 2015

(87) PCT Pub. No.: WO2014/106595
PCT Pub. Date: Jul. 10, 2014

(65) Prior Publication Data
US 2015/0335287 A1    Nov. 26, 2015

(30) Foreign Application Priority Data

Jan. 2, 2013   (EP) .................................. 13150018

(51) Int. Cl.
*A61B 5/00*       (2006.01)
*A61B 5/1477*    (2006.01)
(Continued)

(52) U.S. Cl.
CPC .......... *A61B 5/6833* (2013.01); *A61B 5/1477* (2013.01); *A61B 5/14546* (2013.01);
(Continued)

(58) Field of Classification Search
None
See application file for complete search history.

(56) References Cited

U.S. PATENT DOCUMENTS 5,344,754 A * 9/1994 Zweig ..................... C12Q 1/00
                                                         422/412
5,462,743 A * 10/1995 Turner .................... A61F 13/02
                                                         424/448
(Continued)

FOREIGN PATENT DOCUMENTS

| CA | 2151470 A1 | 6/1994 |
| WO | WO 96/39923 | 12/1996 |
| WO | 2010101621 A1 | 9/2010 |

OTHER PUBLICATIONS

"Back." The Merriam-Webster.Com Dictionary, www.merriam-webster.com/dictionary/back. Accessed Jul. 15, 2021 (Year: 2021).*

(Continued)

*Primary Examiner* — Jacqueline Cheng
*Assistant Examiner* — Jairo H Portillo
(74) *Attorney, Agent, or Firm* — Leason Ellis LLP (57) ABSTRACT

The present invention provides a dermal patch for selectively retaining one or more analyte(s) from a body of a subject comprising: a membrane layer (101) for retaining one or more analyte(s) from a body of a subject, with a first and a second side, wherein the first side is adapted to be in fluid communication with the skin of the subject; optionally holding means for securing the membrane layer in place; an adhesive layer (104); and a backing layer; wherein between the backing layer and the membrane layer (101) there is an expandable layer (103) for applying pressure to the membrane layer.

20 Claims, 6 Drawing Sheets

Cross section of the analysis patch (51) Int. Cl.
*A61B 5/145* (2006.01)
*G01N 33/52* (2006.01)
*A61B 10/00* (2006.01)
*A61F 13/02* (2006.01)
*A61F 13/00* (2006.01)
*A61F 13/84* (2006.01)

(52) U.S. Cl.
CPC ............ *A61B 5/443* (2013.01); *A61B 5/6843* (2013.01); *A61B 10/0035* (2013.01); *A61B 10/0064* (2013.01); *A61F 13/00051* (2013.01); *A61F 13/00055* (2013.01); *A61F 13/00063* (2013.01); *A61F 13/0206* (2013.01); *G01N 33/528* (2013.01); *A61B 2560/0412* (2013.01); *A61F 2013/0028* (2013.01); *A61F 2013/0037* (2013.01); *A61F 2013/0094* (2013.01); *A61F 2013/00544* (2013.01); *A61F 2013/8473* (2013.01)

(56) References Cited

U.S. PATENT DOCUMENTS

| | | | |
|---|---|---|---|
| 5,507,291 A * | 4/1996 | Stirbl | A61B 5/0059 600/301 |
| 5,817,012 A * | 10/1998 | Schoendorfer | A61B 10/0035 600/362 |
| 5,846,559 A | 12/1998 | Hopp | |
| 6,251,083 B1 * | 6/2001 | Yum | A61B 5/14514 600/309 |
| 6,455,065 B1 * | 9/2002 | Hymes | A61K 8/0208 424/400 |
| 7,725,149 B2 | 5/2010 | Peyser et al. | |
| 2004/0019342 A1 * | 1/2004 | Nagasuna | A61F 13/15203 604/385.01 |
| 2005/0106713 A1 * | 5/2005 | Phan | B01L 3/502738 435/287.2 |
| 2005/0129676 A1 * | 6/2005 | Blaschuk | C07D 211/58 424/130.1 |
| 2006/0210616 A1 * | 9/2006 | Linder | A61F 13/02 424/449 |
| 2007/0027383 A1 * | 2/2007 | Peyser | A61B 5/14521 600/347 |
| 2007/0106135 A1 * | 5/2007 | Sloan | A61B 5/14532 600/322 |
| 2007/0179373 A1 * | 8/2007 | Pronovost | G01N 21/78 600/362 |
| 2009/0131858 A1 * | 5/2009 | Fissell | B01D 61/145 604/57 |
| 2010/0209957 A1 * | 8/2010 | Hogan | A61B 10/0096 435/29 |
| 2010/0297205 A1 * | 11/2010 | Wenckens | A61K 9/7084 424/406 |
| 2011/0009847 A1 | 1/2011 | Levinson et al. | |
| 2011/0172507 A1 | 7/2011 | Lademann et al. | |
| 2011/0306677 A1 * | 12/2011 | Kataoka | C09J 7/021 514/729 |
| 2012/0071731 A1 * | 3/2012 | Gottesman | A61B 5/742 600/301 |

OTHER PUBLICATIONS

Examination Report in corresponding Canadian Patent Application No. 2,896,328, dated Nov. 18, 2019. 8 pages.

* cited by examiner

Figure 1 – Patch

Figure 2 – One embodiment of membrane with antibodies

Figure 3 – Cross section of the analysis patch

Figure 4 – Difference in intensity when comparing membranes with and without expandable layers

Figure 5 – Microarray membrane with 16 spots

| SPOT NUMBER | MATERIAL TO PRINT | CONCENTRATION (ug/mL) |
|---|---|---|
| 1 | + Pos Control | 1 |
| 2 | hBD2 | 50 |
| 3 | - Neg Control | (buffer) |
| 4 | IL1a | 50 |
| 5 | IL1a | 5 |
| 6 | hBD1 | 100 |
| 7 | hBD2 | 100 |
| 8 | hBD2 | 100 |
| 9 | hBD1 | 50 |
| 10 | hBD2 | 50 |
| 11 | + Pos Control | 1 |
| 12 | hBD1 | 100 |
| 13 | IL1a | 5 |
| 14 | IL1a | 50 |
| 15 | hBD1 | 50 |
| 16 | - Neg Control | (buffer) |

Figure 6 – Patch

Figure 7 – Kit

DEVICE TO MEASURE ANALYTES IN THE SKIN

CROSS-REFERENCE TO RELATED PATENT APPLICATIONS

This application is a U.S. National Phase Application under 35 U.S.C. § 371 of International Patent Application No. PCT/EP2013/077734, filed Dec. 20, 2013, and claims the priority under 35 U.S.C. Section 119(e) of European Application No. EP 13150018.3, filed Jan. 2, 2013, all of which are incorporated by reference in their entireties. The International Application was published on Jul. 10, 2014 as International Publication No. WO 2014/106595 A1.

FIELD OF THE INVENTION

The present invention relates to dermal patches for selectively retaining one or more analyte(s) from a body of a subject, methods for measuring the concentration of one or more analytes from a body of a subject, as well as kits comprising such patches.

BACKGROUND OF THE INVENTION

Fast development of genomics, transcriptomics, proteomics and regulomics has made it possible to analyze molecular and cellular mechanisms at large scale. One of the important results of these studies has been development of functional genomics and the understanding that cells from different individuals have significant differences in genome structure, gene and protein expression profiles and regulatory mechanisms that control specific cellular functions. This has resulted in an interest in evaluating how effective treatments are on a personal level, in the field of personalized medicine and personalized skin care.

In relation to personalized skin care the claimed effects of anti-wrinkle and anti-aging effects of cosmetic products are typically based on the assumption that these products have similar effect on all individuals. However, this is not the case. Different people and different skin types react differently to cosmetic products, hence the need for personalized skin care.

In personalized skin care and personalized medicine, one way of obtaining samples from subjects for analysis is by the use of transdermal patches, which either actively or passively samples analyte via the skin, where the analyte is transported to the patch e.g. via perspiration or sweat as the carrier medium. The sample can then be analysed by conventional methods to determine the concentration levels of different analytes of interest, which can be used to determine which treatments are most effective for every single person.

WO 96/39923 A1 (to Sudor partners) describes a dermal patch for accumulating moisture expressed from the skin. The focus is on tamperproof drug abuse screening patches. The dermal patch can contain antibodies for specifically binding analytes of interest to the absorbent material of the patch. FIG. 7 of WO 96/39923 A1 shows a dermal patch with two test zones.

WO 96/39923 A1 does not address the problem of reliably and quickly obtaining a result that can be used in personalized medicine and/or personalized skin care.

Consequently, there is still a need in the art for further methods and patches that can reliably determine the level of different analytes, as well as a need for reducing the sampling time necessary to obtain a reliable result.

Additionally, there is a need for reliable and/or improved methods to determine and/or confirm the beneficial effects on the user of, for example, any given active ingredient in a skin care product or a skin medicament for skin diseases.

SUMMARY OF THE INVENTION

The present invention was made in view of the prior art described above, and the object of the present invention is to provide a reliable and/or improved way of determining the level of different analytes while reducing the sampling time necessary.

To solve the problem, the present invention provides a dermal patch for selectively retaining one or more analyte(s) from a body of a subject comprising, e.g. in sequence: a membrane layer (101) for retaining one or more analyte(s) from a body of a subject, with a first and a second side, wherein the first side is adapted to be in fluid communication with the skin of the subject; optionally holding means for securing the membrane layer in place; an adhesive layer (104); and a backing layer; wherein between the backing layer and the membrane layer (101) there is an expandable layer (103) for applying pressure to the membrane layer.

That is, the inventors of the present invention in a first aspect of the invention found that the sampling of analytes could be obtained faster and more reliably by applying pressure to the membrane layer after it has been removably secured to the skin of the subject, thereby ensuring an improved fluid connection between the skin and the membrane.

In some embodiments of the present invention, the holding means (102) is made out of the same material as the membrane layer (101), and where the holding means is not attached to the expandable layer (103).

In some embodiments of the present invention, the expandable layer (103) is for applying pressure and moisture to the membrane layer.

In some embodiments of the present invention, there is a moisture layer for applying moisture to the membrane layer in fluid communication with the membrane layer (101). In some embodiments of the present invention, the moisture layer also functions as a protective layer, and is placed between the expandable layer and the membrane layer, and preferably where the protective layer is placed adjacent to the second side of the membrane layer.

In some embodiments of the present invention, the moisture layer in fluid communication with the membrane layer (101) is the same layer as the expandable layer (103).

In some embodiments of the present invention, the expandable layer (103) contains compressed cellulose.

In some embodiments of the present invention, the backing layer has an aperture that allows liquid added through the aperture to be in fluid communication with the expandable layer and/or the moisture layer.

In some embodiments of the present invention, the area of the expandable layer (103) completely encompass the membrane layer (101) and where the area of the expandable layer (103) is equal to or larger than the area of the membrane layer (101).

In some embodiments of the present invention, the area of the membrane layer (101) is 1 $cm^2$ or less.

In some embodiments of the present invention, the membrane layer (101) comprise one or more distinct capture section(s) with affinity molecule(s) for selectively retaining one or more analyte(s), and in some embodiments the area of the capture section is less than 0.01 $cm^2$, preferably less than 0.003 $cm^2$.

In some embodiments of the present invention, the membrane layer (101) comprises at least four distinct capture sections for selectively retaining the analyte where in each of the at least four distinct capture sections, and in further embodiments at least four different affinity molecules have been immobilized.

In some embodiments of the present invention, the dermal patch is for use in medicine.

Another aspect of the present invention provides a method for measuring the concentration of one or more analytes in a sample comprising the following steps:
a) selecting one or more analytes to be measured;
b) immobilizing onto a membrane in a patch according to the present invention, one or more zones of specific affinity molecules for the selected one or more analytes, and one or more positive and/or negative controls;
c) removably securing the patch of step b) onto the skin of a subject and activate the pressure means;
d) leaving the patch on the skin for the duration of the sampling period;
e) removing the patch from the skin and analysing the membrane to determine the concentration(s) of the selected one or more analytes, and one or more positive and/or negative controls by analysing the one or more zones.

In some embodiments of the present invention, the method additionally comprises the steps:
f) normalising the concentration(s) determined in step e) with the concentration determined for the one or more positive controls
g) comparing the normalised concentration determined under step f) with normalised concentrations from a reference group of subjects.

In some embodiments of the present invention, the one or more analytes to be measured comprise at least one or more of the following group of analytes: extracellular matrix protein (affecting a skin feature), anti-microbial peptides (AMP), interleukins, growth factors and chemokines.

Another aspect of the present invention provides kits for determining the effect of a topical treatment comprising at least two patches according to the present invention. In some embodiments of the present invention, the kit additionally comprises an activation liquid for activating the expandable layer, and wetting the membrane.

BRIEF DESCRIPTION OF THE DRAWINGS

FIG. 7 shows an example of a kit. Under step 1 the kit contains a disposable cleaning towel for cleaning up the area where the two patches are going to be applied. Step 2 can include a container with an active ingredient for topical application and a sticker ring to mark the place where the active ingredient would be applied onto the skin. The active ingredient is left to work for some time, e.g. 60 minutes. Step 3 includes two patches: a control patch which is placed on the cleaned untreated area, and a measuring patch which is placed on the skin treated with the active ingredient from step 2. Step 3 also includes an activation fluid for the expandable membrane and for moisturising the membrane. The patches are left to collect samples from the skin for some time, e.g. 15 minutes. Step 4 involves sticking the control patch and the measuring patch in the designated areas and sending the patches to analysis.

It will be recognized by the person of ordinary skill in the art, given the benefit of this disclosure that certain features shown in FIGS. 1-7 are not necessarily drawn to scale. The dimensions and characteristics of some features in the figures may have been enlarged, distorted or altered relative to other features in the figures to facilitate a better understanding of the illustrative examples disclosed herein.

Figure 1:
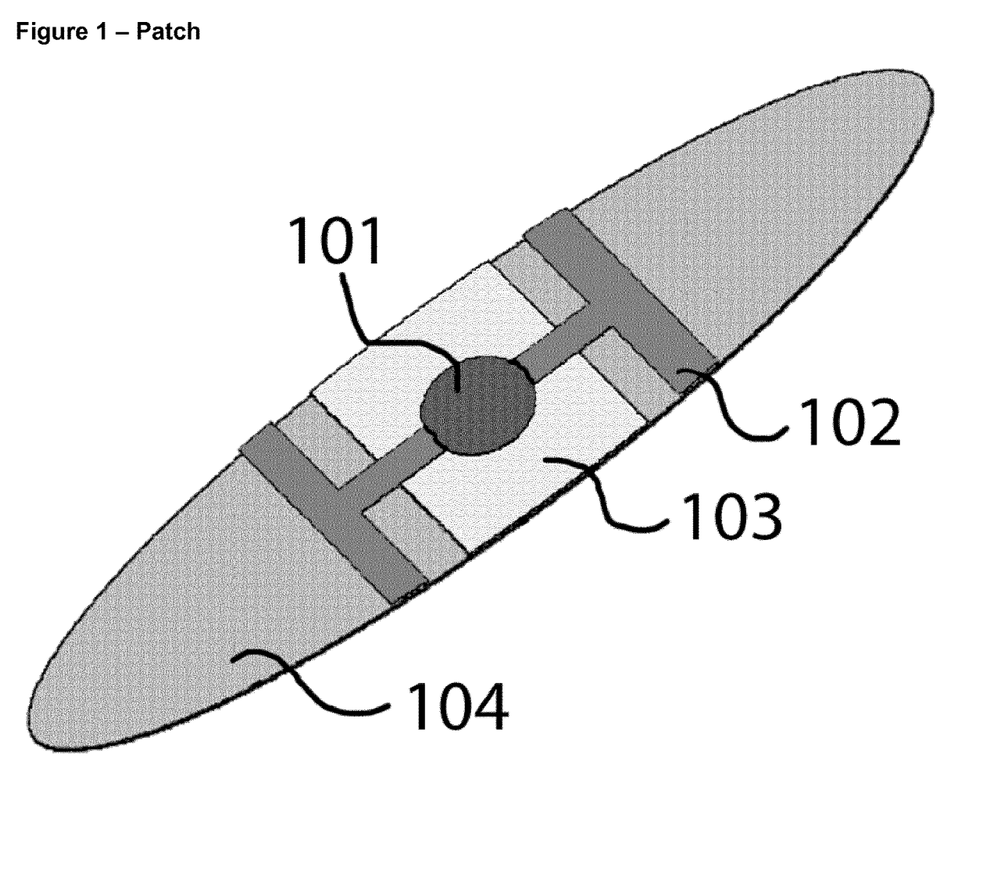
FIG. 1 shows a patch according to some embodiments of the invention with membrane (101), holding means for the membrane (102), expandable layer (103) and adhesive layer (104).
Figure 7:
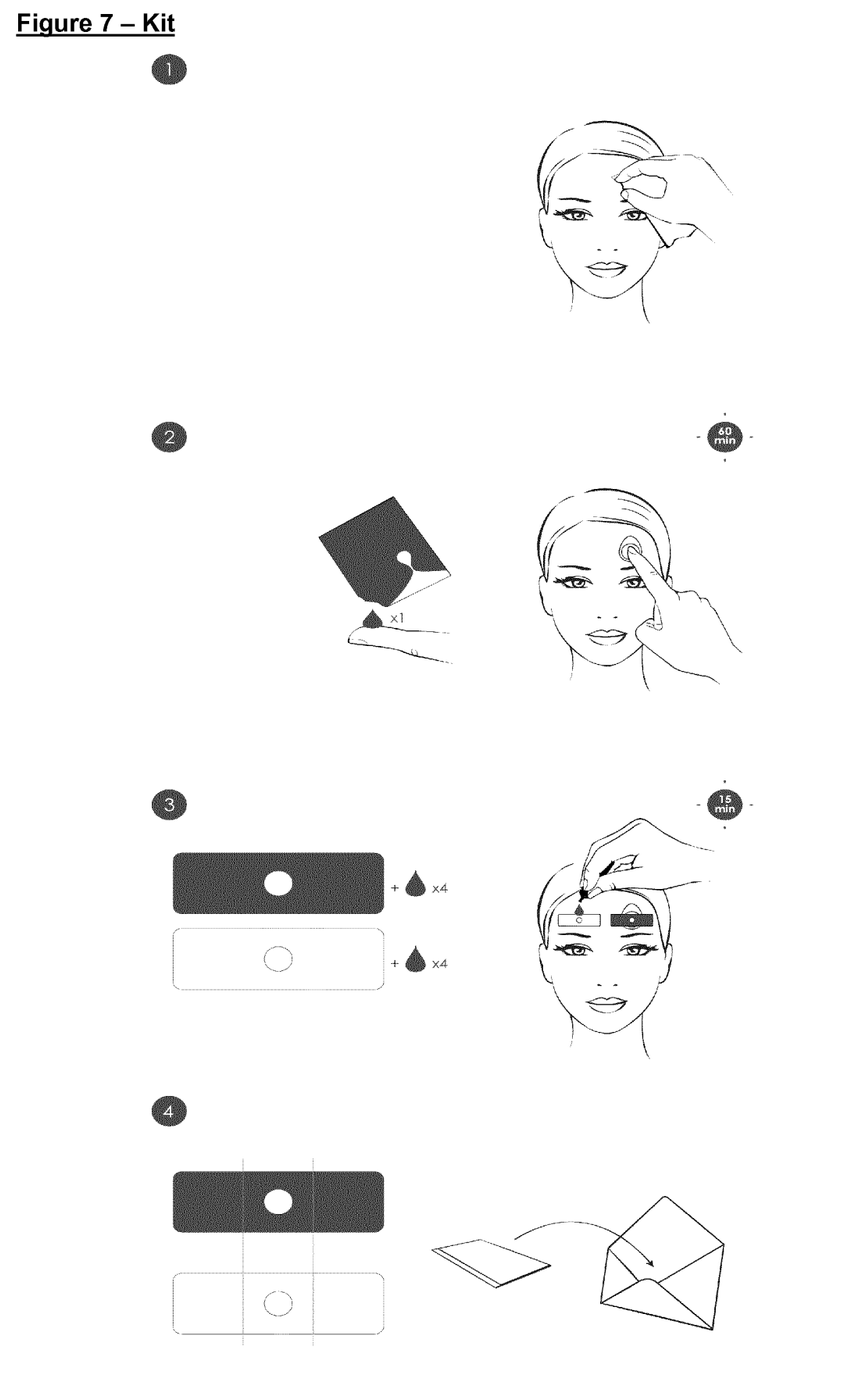

It will further be recognized by the person of ordinary skill in the art that the individual features of the figures may be interchanged to obtain further embodiments, in particular with regards to FIGS. 1 and 7.

DETAILED DESCRIPTION OF THE INVENTION

In describing the embodiments of the invention specific terminology will be resorted to for the sake of clarity. However, the invention is not intended to be limited to the specific terms so selected, and it is understood that each specific term includes all technical equivalents which operate in a similar manner to accomplish a similar purpose.

In the following, reference is made to the accompanying figures, which show by way of illustration how the invention may be practiced.

Figure 6:
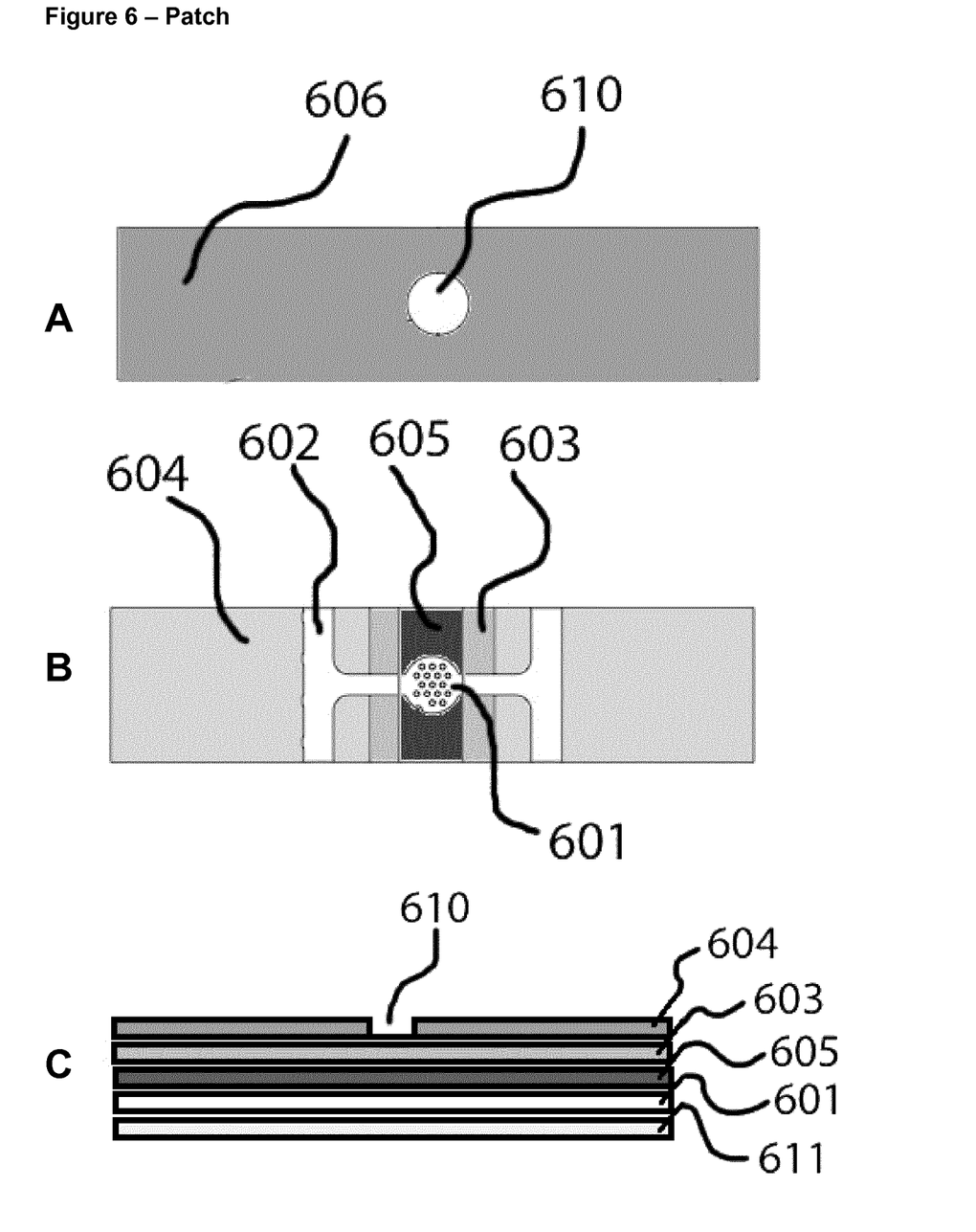
FIG. 6 shows a patch according to some embodiments of the invention, with membrane (601), holding means for membrane (602), expandable layer (603), adhesive layer (604), moisture layer (605), backing layer (606), aperture that allows liquid added through the aperture to be in fluid communication with the expandable layer and/or the moisture layer (610) and a peelable layer to protect the adhesive (611), where (A) is the side facing away from the skin; (B) is the side of the patch that faces the skin; and (C) an cross-sectional view of the patch.

FIGS. 1 and 6 show a schematic of a dermal patch in accordance with certain embodiments of the invention. The dermal patch is for selectively retaining one or more analyte(s) from a body of a subject comprising in sequence:
   a membrane layer (101) for retaining one or more analyte(s) from a body of a subject, with a first and a second side, wherein the first side is adapted to be in fluid communication with the skin of the subject;

optionally holding means for securing the membrane layer in place;
an adhesive layer (104);
a backing layer,
wherein between the backing layer and the membrane layer (101) there is
an expandable layer (103) for applying pressure to the membrane layer.

A dermal patch is a patch that is configured to be releasably fastened to the skin of a subject, and by being in contact with the skin retain one or more analytes. Typically a peelable covering, such as a siliconized release liner protects the membrane and adhesive of the patch. The backing layer and adhesive layer could for example be a porous elastic nonwoven tape with a gentle adhesive. As dermal patches are envisaged diffusion patches, osmosis patches, electrical patches and any other type of patches with enforced diffusion that will collect different analytes present at or near the surface of the skin, such as drugs, drug metabolites, metabolites, glucose, anti-microbial peptides (AMPs), chemokines, interleukins, growth factors and/or hormones. In certain embodiments the analytes are selected from the list consisting of: anti-microbial peptides (AMPs), chemokines and interleukins. In certain embodiments the dermal patch is a diffusion patch, where the diffusion is not enforced.

This retention of analytes can in preferable embodiments be a selective retention, such as by having one or more distinct capture section(s) with affinity molecules, which selectively binds to one or more analyte(s) thereby selectively retaining such analyte(s) of interest. Affinity molecules in general are molecules that have a larger affinity for a particular analyte or class of analytes than other analytes. Most notable examples of such molecules are antibodies (polyclonal and/or monoclonal, and fragments thereof), aptamers, and receptors, as well as other engineered protein scaffolds such known as AdNectin, Affibody, Anticalin, Knottin, DARPin and Kunitz, as well as organic and/or polymeric scaffolds.

The one or more analyte(s) from a body of a subject to be analysed with the patch covers all types of analytes present in the body or on the body. Typically analytes are secreted together with body fluid, and/or body fluid is a carrier medium for the analyte. In some embodiments the analytes are from the skin of the body, such as extracellular analytes present in the skin as well as analytes present on the skin surface, or submerged within the dermal surface, as well as analytes syntetized by keratinocytes or other cells in the skin. In other embodiments relating to e.g. drug wipes, the analytes are the drugs themselves or metabolites thereof, which will be transported with a body fluid to the surface of the skin. The term one or more analyte(s) from a body of a subject is intended to cover all analytes that can be transferred from the skin of the body and onto the membrane layer according to the present invention. In some embodiments the sweat or perspiration released from the skin of the subject will contain the analytes described above, which will be transported via sweat or perspiration to the membrane layer according to the present invention. Exemplary subjects of the present invention are any living creature, such as mammals, for example humans.

The membrane layer (101) should be able to adsorp and/or absorp the analytes, and in certain embodiments the membrane is selected from nitrocellulose, activated Nylon, and/or PVDF, which are suited for immobilisation of in particular capture molecules, including antibodies. The membrane has a first (front) side, which is adapted to be in fluid communication with the skin of the subject, namely that the analyte is able to be transported from the skin of the subject and onto or into the membrane through the first side. The membrane also has a second (back) side, which in some embodiments are in fluid contact with a moisture layer, which ensures that the entire membrane (both the first and second side) is moist thereby improving the fluid communication with the skin. The second side of the membrane could also be only partially in fluid communication with a moisture layer, and still obtain the effect of ensuring that the entire membrane is moist. In preferred embodiments, the membrane layer is permeable to aqueous fluids, such as the body fluid and the aqueous fluid in the moisture layer. In some embodiments the membrane is configured so as not to be expandable.

In some embodiments the membrane layer (101) is not physically attached to the dermal skin patch, but is a separate part. In other embodiments the membrane layer comprises holding means that hold the membrane in place. In some embodiments the holding means are adhesive covering part of the second side of the membrane layer, and in other embodiments the holding means (102) can be attached to the periphery of the membrane layer (101).

The dermal patch comprise an adhesive layer (104), which ensures that the patch can be reversibly fastened to the skin of a subject. The adhesive layer (104) is backed by a backing layer (606) which can be made out of any typical backing layer. In some embodiments the backing layer will not absorb aqueous liquid.

The expandable layer (103) is placed between the backing layer and the membrane layer. It is a layer that can be expanded so as to apply pressure to the membrane layer (101). Examples of an expandable layer are an inflatable material, such as an inflatable pouch, a spring operated device or a swellable material. In some embodiments the expandable layer is not a desiccant, and in some embodiments the material is compressed cellulose, which will swell upon contact with a liquid, such as an aqueous solution, thereby applying pressure to the membrane layer, which will be pressed tightly against the skin of the subject.

In some embodiments, the membrane layer (101) is smaller than the expandable layer (103), and the expandable layer is smaller than the adhesive layer and backing layer.

In some embodiments the holding means (102) of the dermal patch is made out of the same material as the membrane layer (101), which is an example of the holding means (102) being be attached to the periphery of the membrane layer (101). This reduces the components in the patch and simplifies manufacture.

In some embodiments the holding means (102) is not attached to expandable layer (103), but rather attached to the adhesive layer (104). This allows the expandable layer (103), which is also attached to the adhesive layer (104) to expand/move freely over the surface of the membrane layer (101) thereby avoiding pulling and/or distorting the membrane layer so that it is pressed uniformly against the skin.

In some embodiments the expandable layer (103) is for applying pressure and moisture to the membrane layer. One example of an expandable layer which is suitable for both applying pressure and moisture to the membrane layer is compressed cellulose, which expands upon contact with a liquid, such as water, and will also release the water again to components, which it is in fluid contact with, such as the membrane.

The ability of the membrane to be kept moist improves the fluid communication between the skin and the membrane. In some embodiments of the dermal patch, a moisture layer is present for applying moisture to the membrane layer (101). This is also shown on FIG. 6. The moisture layer (605) is a layer in between the expandable layer (103, 603) and the membrane (101, 601). It is beneficial to have a separate moisture layer, when for example the expandable layer is not able to deliver moisture, such as when it is an inflatable plastic pouch. A moisture layer is also beneficial, when the expandable layer is able to deliver moisture, as for example when the expandable layer is a compressed cellulose layer, as the moisture layer can in some embodiments help homogenize the humidity dispersion to the membrane (101) when a liquid, such as aqueous liquid, e.g. a buffer, saline and/or water, is added to the moisture layer. Exemplary embodiments of the moisture layer can be a woven fabric, such as cotton, gaze, and/or cellulose. When the moisture layer is made out of a smooth material it can also function as a protective layer, protecting the membrane from potential damage from the expandable layer and also to evenly distribute the pressure from the expandable layer over the entire membrane. Smooth material such as cellulose and rayon blend absorbent material (e.g. sold as PALL Cellulose and rayon blend absorbent sink, Part no. S70006 and having an average wicking rate of 10 sec/3 cm and a water absorption capacity of 40 µl/cm$^3$) are suitable both as a moisture layer as well as being a smooth protective layer.

In some embodiments the moisture layer in fluid communication with the membrane layer (101) is the same layer as the expandable layer (103). This dual functionality of the expandable layer reduces the number of components in the patch and simplifies manufacture.

In some embodiments the backing layer (606) has an aperture (610) that allows liquid, such as water, to be added through the aperture (610) to be in fluid communication with the expandable layer (103, 603) and/or the moisture layer (605). In this way the dermal patch can be releasably fastened to the skin of the subject and water can be added through the aperture (610) thereby saturating the moisture layer with water. In the embodiments where the expandable layer expands upon contact with water, the water added through the aperture will activate the expandable layer and additionally moisten both the expandable layer and the moisture layer, which in turn will serve as a reservoir of water to keep the membrane wetted throughout the sampling period. In some embodiments the aperture is connected to a blister pack which comprise a predetermined quantity of a liquid, such as water, and which, when ruptured will provide the liquid to the expandable layer through the aperture (610).

In some embodiments the area of the expandable layer (103, 603) completely encompass the membrane layer (101, 601). In some embodiments the area of the expandable layer (103, 603) is equal to or larger than the area of the membrane layer (101, 601). In the embodiments, where the expandable layer covers the membrane layer, and is larger than the membrane layer, it provides an additional reservoir capacity for keeping the membrane wet throughout the sampling period.

Figure 2:
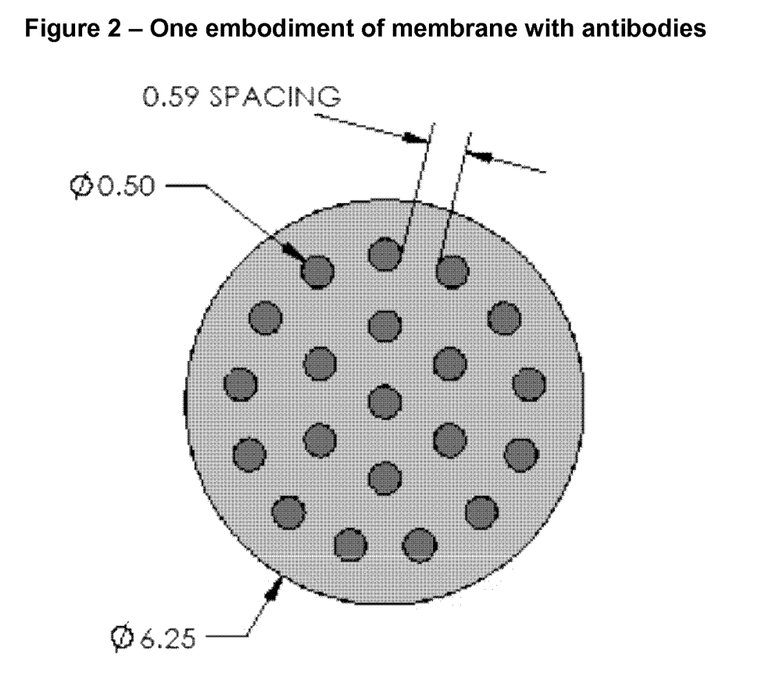
FIG. 2 shows a membrane (101) according to some embodiments of the invention with 20 zones, each around 0.5 mm in diameter, and spaced around 0.59 mm apart on a membrane with a diameter of 6.25 mm and an area of 1.23 cm².
Figure 3:
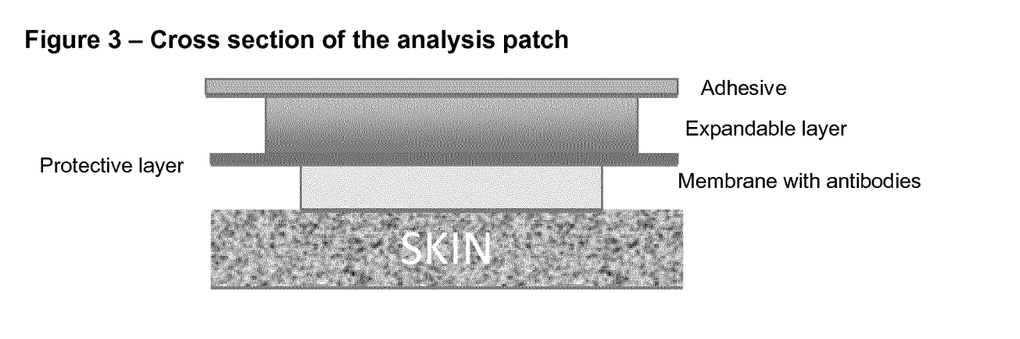
FIG. 3 shows a cross section of a patch according to some embodiments of the invention with an adhesive layer, an expandable layer, a protective layer (moisture layer) and a membrane layer with affinity molecules such as antibodies, placed on the skin.

FIG. 2 shows a membrane layer, which in some embodiments has an area of 1 cm$^2$ or less. This reduces the area for sampling and possible heterogenity effects of a too large sampling area, as well as reducing vulnerability of the patch to movement of the body affecting the area where the patch is applied. In some embodiments the membrane layer has an area of 0.5 cm$^2$ or less, such as less than 0.2 cm$^2$.

As previously described, the membrane is in preferable embodiments adapted for selective retention of analytes, such as by having one or more distinct capture section(s) with affinity molecules, which selectively binds to one or more analyte(s) thereby selectively retaining such analyte(s) of interest. Accordingly, in some embodiments the membrane has at least one distinct capture section consisting of one or more affinity molecules, e.g. one or more antibodies.

A capture section is usually defined by immobilizing (such as crosslinking or conjugating) an affinity molecule to the membrane. This can be done using conventional conjugation chemistry, which is known to the skilled person. Also, when the membrane is made out of a material such as nitrocellulose, activated Nylon, PVDF, and the affinity molecules are protein scaffolds, such as antibodies, then, in some embodiments, specific cross linking or conjugation chemistry is not necessary, as the antibodies will be immobilized on the membrane. On way of making a defined capture section is by dispensing from e.g. a needle, syringe, valve or pipette a specific amount and concentration of the affinity molecule in a spot on the membrane. In some embodiments the affinity molecules spots are made on the first side of the membrane to allow for the fastest and most effective diffusion of analytes to the affinity molecules.

In some embodiments the area of the capture section is less than 0.01 cm$^2$, such as less than 0.003 cm$^2$. Spots with a diameter of 0.1 mm with a corresponding area of around 0.0001 cm$^2$ have been prepared. The small spots, as the capture sections are also called in this description, are advantageous because the smaller the spots are, the smaller is the area in which the analytes of interest accumulates, when binding to the spots containing the specific affinity molecules. This allows for a more concentrated area, which results in a lower sampling time and/or higher reliability in the results, when comparing with a capture section larger than 0.01 cm$^2$. Also the smaller capture area makes it possible to include multiple capture areas with the same affinity molecule in e.g. with same and/or different concentrations to allow for redundancy and/or calibration in the system.

In some embodiments the membrane layer (101, 601) comprise at least four distinct capture sections for selectively retaining the analyte. In some embodiments the number of distinct capture sections are at least 6, such as at least, 8, 10, 12, 16, 18, 20, 25, 30, 40, 50, 70, 100.

In some embodiments the number of different affinity molecules are equal to the number of distinct capture sections.

Figure 5:
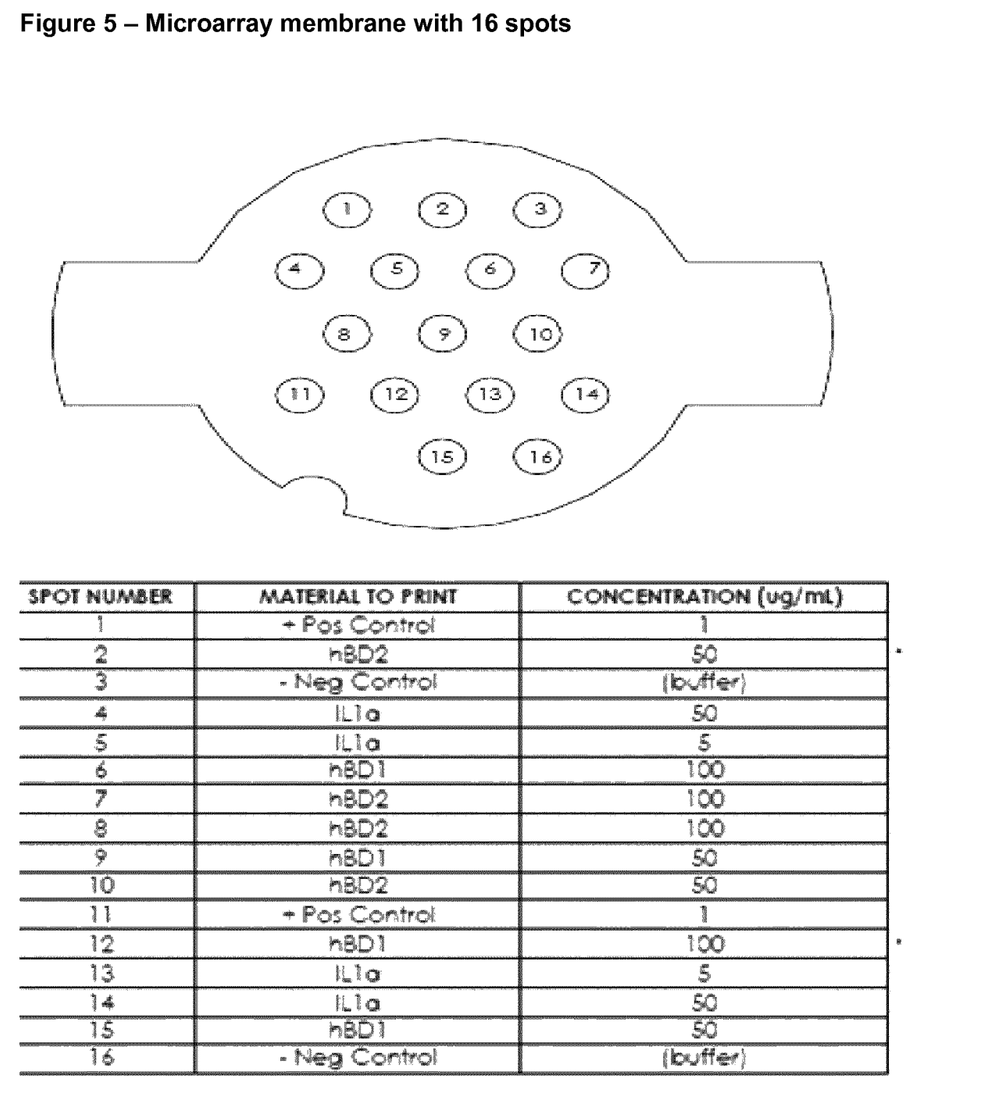
FIG. 5 shows a membrane according to some embodiments of the invention with 16 zones, with corresponding layout of different material to introduce to the zones and the different concentrations.

In some embodiments the number of different affinity molecules are less than the number of distinct capture sections, such as when different concentrations of the same affinity molecule is used on the same membrane, which is shown in FIG. 5.

In some embodiments the number of different affinity molecules is more than the number of distinct capture sections, such as when the patch is used for screening purposes, and a mixture of different affinity molecules are used in a single capture zone. In some embodiments the mixture of different affinity molecules are at least 2, such as at least 8, 10, 12, 16, 18, 20, 25, 30, 40, 50, 70, 100.

In some embodiments the dermal patch according to the present invention is for use in medicine, such as for example in personalized medicine, where the effect of a medical treatment is ascertained using the dermal patch according to the present invention.

In some embodiments the effects of medical treatment that is to be ascertained/monitored using the dermal patch according to the present invention is medical treatment of skin diseases, such as for example inflammatory and infectious skin diseases such as psoriasis, dermatitis.

In some embodiments the dermal patch according to the present invention is for use in ascertaining/monitoring cosmetic treatment, such as for example in personalized skin care, where the effect of a cosmetic treatment is ascertained using the dermal patch according to the present invention.

In some embodiments the cosmetic treatment that is to be ascertained using the dermal patch according to the present invention is cosmetic treatment such as anti-wrinkle treatment, anti-aging treatment, skin scars, keloids, acne, pigmentation disorders, and/or skin inflammation related conditions.

In some embodiments distinct capture sections contain one or more of the following: Positive controls, Negative controls, and normalisation markers, which are analytes, which are secreted at almost the same level in all subjects that can be used to normalize the concentration for comparison with other subjects or reference group of subjects.

The positive control is one or more a capture sections. One example of a positive control is a biotinylated immunoglobulin that can also be used to normalize the immune reaction in the processing of analytical membrane.

The negative control is a capture section without capture antibody, which is illustrative of the "background noise" of the membrane during analysis. When manufacturing the membrane, the negative control area is treated similarly to other capture sections but without the addition of a capture antibody.

The normalization factor is one or more capture sections, containing e.g. an antibody against an antigen that is equally expressed in as many subjects as possible. The skilled person can based on prior art identify one or more candidates for a normalisation factor as a factor that is expressed in as close to equal amounts in different subjects.

Another aspect of the present invention is a method for measuring the concentration of one or more analytes in a sample comprising the following steps:
a) selecting one or more analytes to be measured;
b) immobilizing onto a membrane in a patch according to the present invention one or more capture sections of specific affinity molecules for the selected one or more analytes, and one or more positive controls, negative controls and/or normalisation markers;
c) removably securing the patch of step b) onto the skin of a subject and activate the pressure means;
d) leaving the patch on the skin for the duration of the sampling period;
e) removing the patch from the skin and analysing the membrane to determine the concentration(s) of the selected one or more analytes, and one or more positive and/or negative controls by analysing the one or more zones.

In some embodiments the method additionally comprises:
f) normalising the concentration(s) determined in step e) with the concentration determined for the one or more positive controls and/or normalizing analytes.
g) comparing the normalised concentration(s) determined under step f) with normalised concentration(s) from a reference group of subjects.

In some embodiments the sampling period from the patch is releasably fastened to the skin and the expandable layer activated and until it is removed again is less than 30 minutes. In some embodiments this period is more than 1 minute, such as more than 5 minutes. In other embodiments this period is between 10 and 25 minutes, such as between 15 and 25 minutes. This short period allows the subject to take the test at a clinic, such as a cosmetologist or skin care specialist office, as well as at home.

After the dermal patch has been removed it can be shipped to a laboratory for processing. It is also possible that the patch can be processed on site at e.g. a dermatologist office or beauty clinic with the aid of automated process equipment. In some embodiments the membrane is configured to provide a direct read-out, or a read-out after adding a developing fluid.

Figure 4:
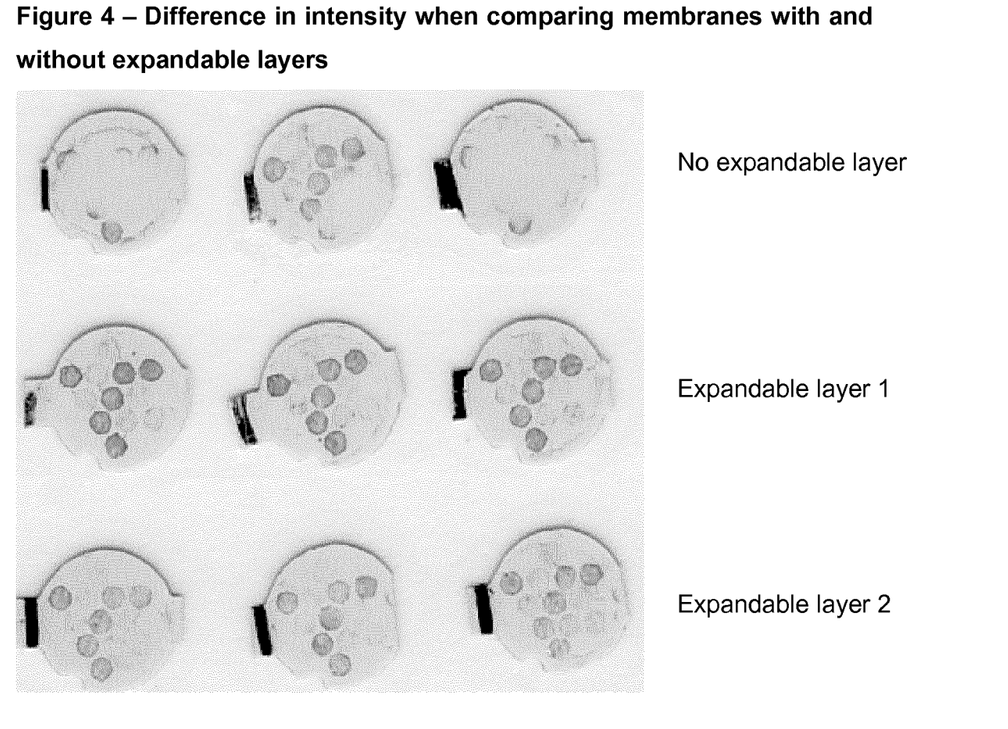
FIG. 4 shows a difference in intensity when comparing membranes with and without expandable layers. "Expandable layer 1" uses one sheet of compressed cellulose and "Expandable layer 2" uses two sheets of compressed cellulose.

Many ways of analysing the membrane for binding of analyte to the affinity molecules exists in the art. In some embodiments the binding event will be visualised using a colorimetric immunoassay (such as ELISA analysis) either with or without amplification, such as by using a biotin-streptavidin assay. The intensity of the capture sections correspond to the concentration of the analyte, and such intensity can be quantitatively determined by scanning the membranes and using analysis software. Examples of membranes that have been analysed using a colorimetric assay are shown in FIG. 4. In some embodiments fluorescence, immunogold or nanoparticles based detection techniques will be used to quantify bound analytes.

In some embodiments of the present invention the one or more analytes to be measured comprise at least one or more of the following group of analytes: extracellular matrix protein (affecting a skin feature), AMP, interleukins, growth factors and chemokines. Alterations in the patterns of these regulatory proteins in the skin of the individual before and after treatment(s) can be compared and a conclusion can be reached as to the effectiveness of the treatment. In some embodiments part of the skin is treated with an agent, and two dermal patches are applied, one on top of the treated area, and a second next to the treated area, such as 1, 2, 3, or 4 cm or more from the treated area.

In some embodiments of the present invention a kit for determining the effect of a topical treatment is provided. Here one or more active ingredient(s) will be topically applied to an area of interest on the skin surface. After the active ingredient have been applied, and allowed ample time to work, one patch is placed over the treated area, and another patch is placed over an untreated area. Accordingly in some embodiments of the present invention the kit comprises at least two patches according to the present invention. In some embodiments of the present invention the kit also provides an activation liquid for moisturising the membrane and/or for activating the expandable layer, e.g. in the embodiments, where the expandable layer swells upon contact with water, such as e.g. compressed cellulose. The activation liquid is in some embodiments aqueous, such as water, or isotonic water. In other embodiments the activation liquid is aqueous PBS buffer.

FIG. 7 shows an example of a kit. Under step 1 the kit contains a disposable cleaning towel for cleaning up the area where the two patches are going to be applied. Step 2 can include a container with an active ingredient (e.g. cream drug, product, etc.) for topical application and a sticker ring to mark the place where the active ingredient would be applied onto the skin. The active ingredient is left to work for some time, e.g. 60 minutes. Step 3 includes two patches: a control patch which is placed on the cleaned untreated area, and a measuring patch which is placed on the skin treated with the active ingredient from step 2. Step 3 also includes an activation fluid for the expandable membrane and for moisturising the membrane. The patches are left to collect samples from the skin for a some time, e.g. 15 minutes. Step 4 involves sticking the control patch and the measuring patch in the designated areas and sending the patches to analysis.

In some embodiments the active ingredients applied topically to the skin could be e.g. retinoic acid and/or progesterone, and the analytes to be detected are at least one analyte selected from one or more of the groups comprising of:
  a) a first set of analytes indicative of the compound or composition is affecting skin regeneration, wherein said first set of analytes is at least one chemokine such as CCL5, CCL27 and CXCL1 and/or at least one AMP such as DEFB1, DEFB103A, DEFB4A, CAMP, DCD, S100A7, and RNASE7, and/or at least one interleukin such as IL1.
  b) a second set of analytes indicative of said compound or composition is affecting skin elasticity and/or skin strength, wherein said second set of analytes is at least one AMP such as DEFB1, DEFB103A, DEFB4A, CAMP, DCD, S100A7, and RNASE7.

The detection device of the invention may detect one or more AMPs and/or one or more chemokines and/or interleukins from each set of biomarkers. The specific set of biomarkers to be measured may depend on which cosmetic compound or composition is to be evaluated. The reason being that the correlation between an ECM and an AMP may vary depending on the compound or composition applied to the skin.

The effect of the expandable layer can be seen in example 4, which compares the quantitative intensity and standard deviation of the bound analytes in a patch according to FIG. 6 with and without the expandable layer.

The difference in intensity can also be ascertained qualitatively by comparing the patch of FIG. 6 with and without an expandable layer, the results shown in FIG. 4, where it is clearly seen that the intensity is better in the membranes with the expandable layer than without the expandable layer.

When describing the embodiments of the present invention, the combinations and permutations of all possible embodiments have not been explicitly described. Nevertheless, the mere fact that certain measures are recited in mutually different dependent claims or described in different embodiments does not indicate that a combination of these measures cannot be used to advantage. The present invention envisages all possible combinations and permutations of the described embodiments.

EXAMPLES

Materials and Methods

Materials
  Cell culture plastic: 48-well; (Greiner)
  hBD-1 ELISA-kit (PeproTech, Cat.nr 900-K202)
  hBD-2 ELISA-kit (PeproTech, Cat.nr 900-K172)
  IL-1a ELISA-kit (PeproTech, Cat.nr 900-K11)
  Membrane prototypes: Hydro-C Extra nitrocellulose membrane (Amersham Cat. Nr RPN2020E; material nr 1212424) with spotted capture antibodies:
  hBD-1 capture antibody (PeproTech, Cat.nr 900-K202)
  hBD-2 capture antibody (PeproTech, Cat.nr 900-K172)
  IL-1a capture antibody (PeproTech, Cat.nr 900-K11)
  Catalyzed Signal Amplification (CSA) System (Dako, Cat. Nr K-1500)
  Bovine serum albumine (BSA), (PAA Cat. Nr K41-001)
  1×PBS
  Tween-20 (AppliChem, Cat.nr A4974,0500)
  MilliQ water
  Forceps for membrane handling
  Wash Buffer—1×PBS (1.06 mM $KH_2PO_4$, 2.97 mM $Na_2HPO_4$-$7H_2O$, 155.17 mM NaCl, pH 7.2)-0.1% Tween+1% BSA
  Blocking agent: 5% BSA in 1×PBS (filter BSA solution)
  Standard protein (positive control) and detection antibody are diluted in diluent.
  Diluent—1×PBS-0.05% Tween+1% BSA Example 1

Preparing the Analysis Patch Containing hBD1 and IL1a Capture Antibodies

The analysis patch was produced using capture antibodies from a Human IL-1a ELISA Development Kit (Catalogue no. 900-K11 from PeproTech) at a concentration of 50 µg/ml; and Human HBD 1 ELISA Development Kit (Catalogue no. 900-K202 from PeproTech) at a concentration of 50 µg/ml. As Negative control 1×PBS-20% Glycerol was used, and as positive control hBD1 detection antibody 50 µg/ml was used. The capture antibodies were spotted onto the membrane using a non-contact dispersing system (Bio-Dot AD 3400 with BioJet plus dispersing system). In this example the spot volume dispersed was 30 nl.

Example 2

Exposure of the Analysis Patch to the Skin

Place the analysis patch on the skin (control for tight attachment, membrane has to have a good contact with the skin) and wet the patch (expanding layer, analysis membrane) with 150 µl 1×PBS. Keep the patch in contact with the skin for 15 min. Remove patch and separate membrane from the rest of the patch. Place membrane into 48-well plate well with the protein side up.

Example 3

Visualisation of Analyte Bound to the Membrane

In order to visualise the analyte bound to the membrane after exposure to the skin the membrane is incubated with detection antibodies in the following manner. Wash membranes 3×5 min in 200 µl wash buffer. Prepare detection antibody solution mix, hBD-1, 1:2000 and IL-1a, 1:1000 in diluent buffer. Incubate membranes with detection antibody solution 45 min at room temperature RT on shaker. Wash membranes 5×5 min with 200 µl wash buffer each time.

The signal is amplified using the Catalyzed Signal Amplification (CSA) System (Dako) in the following manner. Prepare Streptavidin-Biotin complex: 1 drop (one drop is ~40 µl) Streptavidin Biotin Complex Reagent A, 1 drop Streptavidin Biotin Complex Reagent B and up to 1 ml Streptavidin Biotin Complex Reagent solution. Dilute prepared Streptavidin Biotin Complex Reagent for 1/9 in 1×PBS-0.05% Tween. Pipet in each well 150 µl solution and incubate for 15 min room temperature (RT). Wash membranes 3×5 min in 200 µl wash buffer. Incubate membranes with Amplification reagent solution: 1/8 Amplification regent, 7/8 1×PBS-0.05% Tween. Pipet in each well 150 µl solution. Incubate for 15 min room temperature (RT) following washing 3×5 min in 200 µl in wash buffer. Incubate with diluted Strepdavidin-HRP solution: 1/8 Strepdavidin-HRP; 7/8 1×PBS-0.05% Tween. Pipette in each well 150 µl solution and incubate for 15 min at RT.

Wash membranes twice with 200 μl wash buffer following one wash with 1×PBS/0.05% Tween. Incubate with 100 μl DAB (3,3'-diabenzidine tetrahydrochloride (added 0.8% $H_2O_2$; 20 μl 0.8% $H_2O_2$ for 1 ml DAB) for 15 min. Stop reaction with MilliQ water (~200 μl per well): add MilliQ water in to the wells and aspirate instantly. Wash membranes with MilliQ water 10×2 min (200 μl at once).

The membranes are left to dry in air and then the colour intensity, proportional to the concentration of the analytes were determined using image analysis software (Dige Imager, GE Healthcare) according to the protocol in the software to quantify amount of bound analyte. The membranes were scanned using a document scanner at 1200 dpi (Canon Scan LiDE 600F). The images obtained were analyzed using microarray and dot/slot blot analysis software Image Quant TL V2005 (GE Healtcare). The amount of analytes bound to capture antibodies was calculated using standard calibration curve. In the calibration procedure membranes with capture antibodies were incubated in solutions containing different concentration of analytes following processing using standard protocol. Based on obtained results calibration curve was constructed and used for determining amount of analytes bound to capture antibody.

Example 4

Comparing Results from Patches with and without Expandable Material

Comparison of analysis results obtained using the analysis skin patches with and without expandable layer shows that expandable layer improves the reproducibility and quality of analysis results, as evident from FIG. 6 and the below table.

The table shows the effect of the expandable layer on the detection level and variation of the Patch analysis results. Patches with and without expandable material (in the patch without expandable material, the expandable material was exchanged with a non-expandable material) having two different capture antibodies, IL-1a, hBD1 (each of the antibodies were represented by 6 spots) were each wetted with PBS (150 μl) and after being releasably fastened to 4 individuals. The membranes were exposed for 15 minutes following identical processing. Intensity of immunostaining of each spot was analyzed using image analyzer and average intensity, standard deviation and standard deviation % were calculated.

|  | Average of six spots of IL1a | Standard deviation in % |
|---|---|---|
| Patch with expandable material | | |
| Person no. 1 | 105132 ± 9521 | 9% |
| Person no. 2 | 135358 ± 7835 | 6% |
| Person no. 3 | 121045 ± 7615 | 6% |
| Person no. 4 | 150986 ± 7063 | 5% |
| Patch without expandable material | | |
| Person no. 1 | 53332 ± 11085 | 21% |
| Person no. 2 | 84085 ± 22905 | 27% |
| Person no. 3 | 86589 ± 20650 | 24% |
| Person no. 4 | 79966 ± 21615 | 27% |

It can be seen from the readings of the patches containing an expandable layer resulted in significantly higher value of analytes, and resulted in significantly lower standard deviation and standard deviation %, whereas the patches without expandable material resulted in significantly lower average readings, and higher standard deviations.

This higher sensitivity and lower variation of analysis from the patches with the expandable layer is related to firm and homogenous contact of the membrane with the skin due to constant pressure created by the expandable layer.

The invention claimed is:

1. A dermal patch comprising layers in the following order:
    a membrane layer (101, 601) for retaining one or more analyte(s) from a body of a subject with skin, the membrane layer (101, 601) having a first and a second side, wherein the first side is in fluid communication with the skin of the subject, wherein the membrane layer (101, 601) has an area and is non-expandable, and wherein the membrane layer (101, 601) comprises one or more distinct capture section(s) with affinity molecule(s) for selectively retaining one or more analyte (s);
    an expandable layer (103, 603), wherein said expandable layer applies a pressure, which is evenly distributed over the entire membrane layer;
    an adhesive layer (104); which ensures that the patch can be reversibly fastened to the skin of a subject;
    a backing layer (606);
    wherein said membrane layer is facing the skin and said backing layer (606) is facing away from the skin; and
    wherein said adhesive layer is protected by a peelable layer (611).

2. The dermal patch according to claim 1 wherein the expandable layer (103, 603) presses and moisturizes the membrane layer (101, 601).

3. The dermal patch according to claim 1 wherein a moisture layer (605) is in fluid communication with the membrane layer (101, 601).

4. The dermal patch according to claim 3, wherein the moisture layer (605) is in fluid communication with the membrane layer (101, 601) and is the same layer as the expandable layer (103, 603).

5. The dermal patch according to claim 1 wherein the expandable layer (103, 603) contains compressed cellulose.

6. The dermal patch according to claim 1 wherein the backing layer (606) has an aperture (610) that allows liquid added through the aperture (610) to be in fluid communication with the expandable layer (103, 603) and/or the moisture layer (605).

7. The dermal patch according to claim 6 wherein the backing layer will not absorb aqueous liquid.

8. The dermal patch according to claim 1 wherein the expandable layer (103, 603) has an area that completely encompasses the membrane layer (101, 601) and wherein the expandable layer (103, 603) has an area that is equal to or larger than the area of the membrane layer (101, 601).

9. The dermal patch according to claim 1 wherein the area of the membrane layer (101, 601) is 1 $cm^2$ or less.

10. The dermal patch according to claim 1 wherein the membrane layer (101, 601) comprise at least four distinct capture sections for selectively retaining the one or more analyte wherein each of the at least four distinct capture sections immobilize at least four different affinity molecules.

11. The dermal patch according to claim 1 for use in medicine.

12. A method for measuring the concentration of one or more analytes in a sample comprising the following steps:
   a) selecting one or more analytes to be measured;
   b) immobilizing onto a membrane in a patch according to claim 1 one or more zones of specific affinity molecules for the selected one or more analytes, and one or more positive and/or negative controls;
   c) removably securing the patch of step b) onto a subject's skin and activating the expandable layer of the patch;
   d) leaving the patch on the skin for a period of time;
   e) removing the patch from the skin and analysing the membrane to determine the concentration(s) of the selected one or more analytes, and one or more positive and/or negative controls by analysing the one or more zones.

13. A method according to claim 12 additionally comprising:
   f) normalising the concentration(s) determined in step e) with a concentration determined for the one or more positive controls; and
   g) comparing the normalised concentration determined under step f) with normalised concentrations from a reference group of subjects.

14. The method according to claim 12 wherein the one or more analytes to be measured comprise at least one or more of the following group of analytes: extracellular matrix protein, anti-microbial peptides (AMP), interleukins, growth factors and chemokines.

15. A kit for determining the effect of a topical treatment comprising at least two patches according to claim 1, and an activation liquid wherein the activation liquid activates the expandable layer and wets the membrane layer.

16. The dermal patch according to claim 1, further comprising a membrane holding layer (102, 602).

17. The dermal patch according to claim 16, wherein the membrane holding layer (102, 602) is made out of the same material as the membrane layer (101, 601), and where the membrane holding layer (102, 602) is not attached to the expandable layer (103, 603).

18. The dermal patch according to claim 16, wherein the membrane holding layer (102, 602) is an adhesive.

19. The dermal patch according to claim 1 wherein the one or more distinct capture section(s) has an area that is less than 0.01 cm$^2$.

20. The dermal patch according to claim 1 wherein the one or more distinct capture section(s) has an area that is less than 0.003 cm$^2$.

* * * * *